United States Patent
Nowland

(10) Patent No.: US 8,156,786 B2
(45) Date of Patent: Apr. 17, 2012

(54) METHOD OF TESTING A SOIL SPECIMEN

(76) Inventor: Bradley T. Nowland, N Fort Myers, FL (US)

( * ) Notice: Subject to any disclaimer, the term of this patent is extended or adjusted under 35 U.S.C. 154(b) by 125 days.

(21) Appl. No.: 12/801,787

(22) Filed: Jun. 25, 2010

(65) Prior Publication Data

US 2011/0314895 A1    Dec. 29, 2011

(51) Int. Cl.
*G01N 33/24* (2006.01)
(52) U.S. Cl. ............... 73/19.01; 73/19.09; 73/23.2
(58) Field of Classification Search .............. None
See application file for complete search history.

(56) References Cited

U.S. PATENT DOCUMENTS

| | | | | |
|---|---|---|---|---|
| 5,140,845 A | * | 8/1992 | Robbins | 73/19.03 |
| 5,792,423 A | * | 8/1998 | Markelov | 422/83 |
| 6,143,573 A | * | 11/2000 | Rao et al. | 436/180 |
| 6,286,375 B1 | * | 9/2001 | Ward | 73/863.12 |
| 7,398,703 B2 | * | 7/2008 | Nath et al. | 73/864.81 |

* cited by examiner

*Primary Examiner* — Hezron E Williams
*Assistant Examiner* — Mark A. Shabman

(57) ABSTRACT

The inventive method is designed to test contaminants in soil that is contaminated with petroleum related products. The method involves the use of a container that will separate soil into a head space for analysis. The container consists of two halves and the container is partially filled with a soiled dirt specimen. The container is then hermetically sealed against the environment by way of a cover snapped over the container rim. The container with the contaminated specimen therein is allowed to accumulate a vapor head space within a certain time period. An instrument will puncture a sealed orifice in the top cover and a sample of the vapor is withdrawn for further analysis.

4 Claims, 2 Drawing Sheets

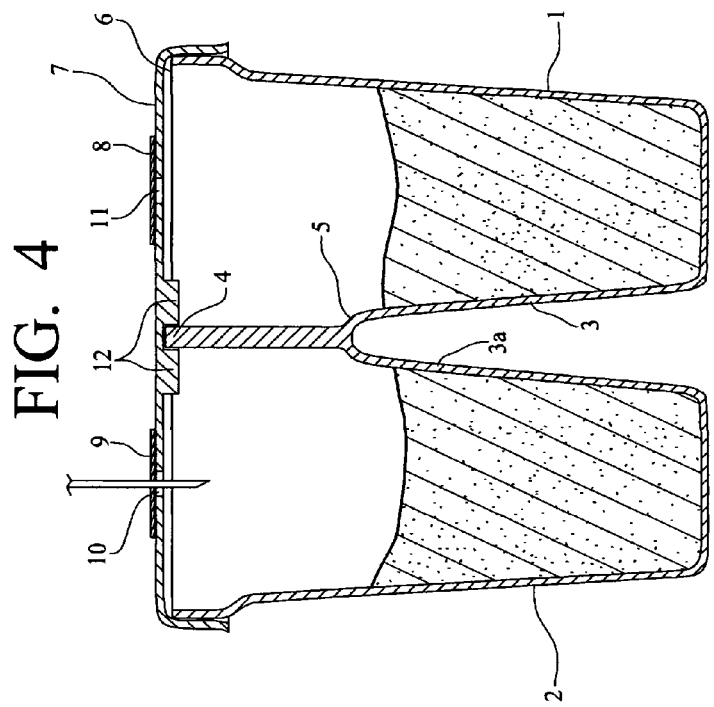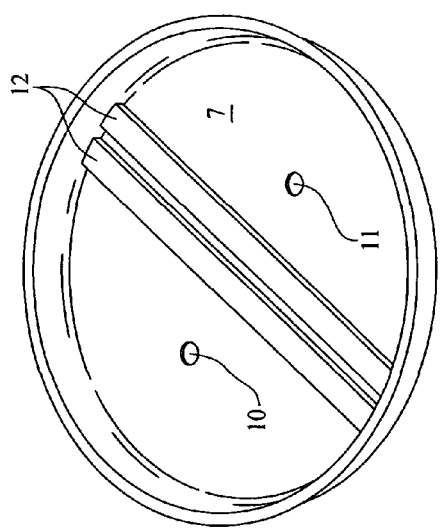

METHOD OF TESTING A SOIL SPECIMEN

BACKGROUND OF THE INVENTION

It is known that underground gasoline tanks can develop a leak. It is also known that car or truck wrecks can spill gasoline or diesel fuel that contaminate the ground. In order to proceed with a cleanup or comply with environmental standards, it must be determined what the damages in the soil are and to what extent. Therefore, it is desirable to have a simple way to find out the extent of the contamination and, of course, the kind of contamination.

BRIEF DESCRIPTION OF THE INVENTION

The inventive concept involves a special container that is partially filled with a soil specimen. The container is so constructed that the soil specimen is divided into two parts so that two tests can be performed using the same container. A top of the container is hermetically sealed from the environment and the two specimen within the container are hermetically sealed from each other.

BRIEF DESCRIPTION OF THE DRAWINGS

FIG. 3 illustrates an underside view of the container cover;
FIG. 4 is a cross section through the container showing the two compartments.

DETAILED DESCRIPTION OF THE INVENTION

Figure 2:
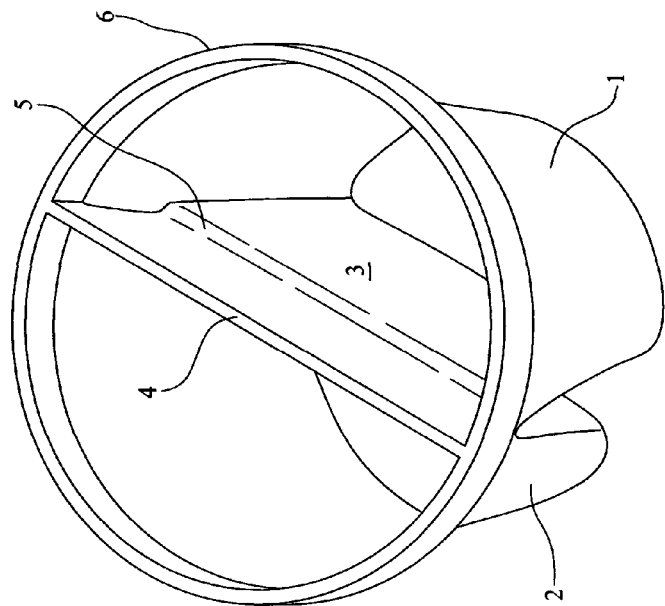
FIG. 2 is a perspective view of the container 1, with the top open.
Figure 1:
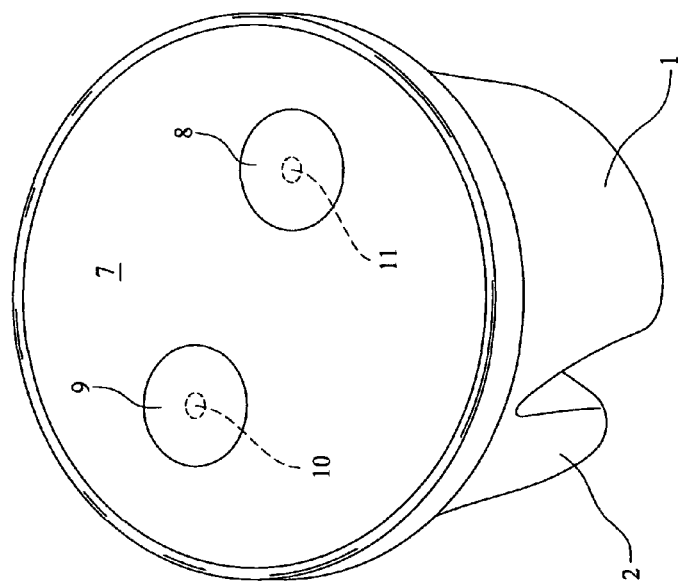
FIG. 1 is perspective view of the container.

The inventive concept involves the method for extracting and analyzing virtually any sample or specimen of the soil which may be contaminated with pollutants, toxics or other impurities. The method involves the following steps:

The container shown in FIG. 1 is used to extract soil from a contaminated area. The contaminants can be spilled gasoline or spilled diesel fuel. The OVT (Organic Vapor Test) cell/container is filled with the soil to be tested. This is accomplished by partially filling the two halves 1 and 2 of the test container with the soiled dirt or earth. The container is then covered by a cover 7 which then hermetically seals the container against the environment and also hermetically seals the two halves relative to each other. The cover 7 has two orifices 9 and 8 and the orifices are covered by a seals 10 and 11, respectively. FIG. 2 illustrates a perspective of the opened container. Again the two compartments 1 and 2 are shown and the respective walls of the of the two containers are merging into single upstanding wall 4. This upstanding wall is important because, as shown in FIG. 3, which shows the underside of the cover 7. There are shown two ridges 12 on the underside of the cover 7 and when the cover 7 is snapped over the rim 6 of the basic container, the upstanding wall 4 will hermetically seal the both compartments 1 and 2 against the general environment and against each other because the upstanding wall will seat within the two ridges 12.

The inventive method involves the following steps:

If a contaminated soil has to be tested, the container with its two halves 1 and 2 are partially filled with the contaminated specimen. The cover 7 is snapped over the basic container to seal both compartments 1 and 2 against each other. The container is retired for a certain period of time wherein there is a build up or accumulation of a head space vapor in the vacant spot above the specimen in both halves of the container. This time period may be anywhere between 5 to 30 minutes at a temperature range of 68° F. to 90° F. The accumulated headspace vapor is then tested with a calibrated organic vapor analyzer (OVA) equipped with a flame ionization detector (FID) or equivalent instrument. The accumulated headspace vapor is extracted from the headspace below the sealed cover by punching an extraction needle through one of the sealed orifices 10 or 11. The other chamber is then tested by punching with an instrument through the other sealed orifice and is tested with a GAC filter to adsorb or filter out all the related hydrocarbons or other volatile contaminant vapors and allow naturally occurring methane gas to be recorded. The filtered reading is then subtracted from the total reading to obtain a methane-corrected reading which is considered representative of the hydrocarbon or any other volatile contaminant vapor content of the soil sample for field general screening purposes.

It can now be seen that a method has been disclosed by conducting a quantitative field soil headspace analysis to aid in the identification and delineation of petroleum related products and other contaminants (mainly volatile aromatic polycyclic hydrocarbons and dry cleaning solvents) in soil and groundwater samples.

What I claim is:

1. A method for analyzing petroleum related contaminants in a soil comprising the steps of:
    providing a container,
        said container having two separate compartments therein;
    scooping up a contaminated soil specimen and partially filling each of said two compartments with said specimen;
    placing a cover on said container to hermetically seal said container against the environment and hermetically seal said two compartments from each other;
        wherein said cover comprises two sealed orifices on allowing access to each of said compartments independently;
    allowing said container sufficient time to develop a vapor head space above each of said partial soil specimens within each compartment; and
    punching through a first one of said sealed orifices and extracting a vapor sample from said head space in a first sealed compartment for a further analysis.

2. The method of claim 1, wherein said analysis includes the testing of said head space vapor with a calibrated organic vapor analyzer instrument.

3. The method of claim 1 further comprising,
    extracting a head space sample from said container by punching through the second sealed orifice and extracting a vapor sample from said head space for another specified analysis in another specified analysis.

4. The method of claim 3, wherein said another specified analysis comprises testing said head space vapor in the second sealed compartment by punching with an instrument through said second sealed orifice and testing the obtained vapor with a GAC filter to either adsorb or filter out all of the related hydrocarbons or other volatile contaminant vapors and allow naturally occurring methane gas to be recorded.

* * * * *